United States Patent [19]

Lung et al.

[11] Patent Number: 5,061,639
[45] Date of Patent: Oct. 29, 1991

[54] LIQUID DISPENSER ACCURACY VERIFICATION METHOD

[75] Inventors: Kaki R. Lung; John S. Fox, both of Hockessin, Del.; Alex J. Chanin, Philadelphia, Pa.

[73] Assignee: E. I. duPont de Nemours and Company, Wilmington, Del.

[21] Appl. No.: 446,773

[22] Filed: Dec. 6, 1989

[51] Int. Cl.$^5$ ............................................. G01N 30/00
[52] U.S. Cl. ..................................... 436/164; 436/10; 422/100; 422/102; 422/106; 422/99
[58] Field of Search .................. 436/164, 10; 422/100, 422/106, 99

[56] References Cited

U.S. PATENT DOCUMENTS 4,354,376 10/1982 Greenfield ................................ 73/1

OTHER PUBLICATIONS

Condensed Chemical Dictionary, pp. 262, 848, 982–983, © 1981.

Primary Examiner—David L. Lacey
Assistant Examiner—Abanti B. Singla

[57] ABSTRACT

In the method of this invention, dispensed volume is calculated from the ratio of the absorbance values for a sample delivered by a precisely calibrated pipette and the sample dispensed by an automated pipette. This links a gravimetric method of calibration to a colorimetric method.

8 Claims, 12 Drawing Sheets

LIQUID DISPENSER ACCURACY VERIFICATION METHOD

FIELD OF THE INVENTION

This invention relates to a method of determining the accuracy of a liquid dispenser. More particularly, this invention relates to a method of use of robotic equipment in the processing of micorotiter-plate based assays. The method permits diagnostic instruments using absorbance type measurements and laboratory robots in the analysis of samples to verify the accuracy of the dispensing portion of the robot. This method finds particular use in diagnostic instruments analyzing samples which contain viruses (or antibody to the virus) of infectious diseases. Typical of such infectious diseases are the human immunodeficiency virus Type-1(HIV-1).

BACKGROUND OF THE INVENTION

Various diagnostic instruments are known which are used in the detection of infectious disease agents and antibodies thereto. One such instrument uses a microtiter-plate based enzyme linked immunoabsorbant assay (ELISA). The development of microtiter-plate ELISA methods allows the processing of a large number of samples (typically 96 wells per plate) simultaneously. A common problem in the use of the microtiter-plate based ELISA method is the tracking of sample identity. The wells in a microtiter plate are closely spaced. When a blood sample is manually transferred from a sample tube to one of the closely spaced wells, it can easily be misplaced into a neighboring well.

Several laboratory and robotic systems have been developed for the purpose of processing microtiter plates. These devices are designed to increase laboratory throughput and many of these devices also provide positive sample identification through the use of barcode labels.

For example, the Zymate robot (Zymark Corporation, Hopkinton, Mass., U.S.A.) has been adapted for the processing of the microtiter plates in the research laboratory. Another laboratory automation device that has been in use in many clinical laboratories is the Hamilton MICROLAB-AT (Hamilton Corporation, Reno, Nev., U.S.A.).

The Hamilton MICROLAB-AT, which is also supplied by DuPont as an OEM equipment known as the SUMMIT TM, is capable of performing the following functions:

1) Reading the barcode labels on each of the 96 sample tubes placed in a tube rack.
2) Adding a precisely measured amount of reagent to each of the 96 wells on the microtiter plate.
3) Transferring a precisely measured amount of sample from the sample tube to the corresponding well on the microtiter plate.
4) Mixing the reagent with the sample and performing any dilution, if required.

In order to minimize the hazards involved in the transfer of human serum which may contain infectious disease agents, the DuPont SUMMIT uses disposable pipets which are ejected into a biohazardous bag after each run. The use of disposable pipets, however, makes the verification of sample accuracy and precision more difficult.

The relatively small size of the wells on the microtiter plate (typically 300 uL per well) requires the precise delivery of a minute amount of sample (typically 10 uL or less). Inaccuracies in the delivery of samples will lead to erroneous results that may endanger public health and the safety of blood supplies. In order to safeguard the accuracy of the ELISA results, the volume delivered by the automated devices must be routinely verified.

Typically, the verification of the volumetric accuracy of a device is accomplished by weighing a sample of pure water transferred by the device. Although this method is a satisfactory procedure for the verification of the delivery of relatively large sample sizes (100 uL or more, i.e. 0.1 g in weight), it is not a satisfactory method for the verification of volumes in the range of 5-10 uL. Sample sizes in the range of 5-10 uL are often required for many microtiter-plate based ELISA methods.

When attempts are made to weigh a 10 uL (or 0.01 g) sample of pure water, the surface tension of water will often lead to the incomplete transfer of the liquid from the pipet tip to the microtiter plate. Moreover, evaporative loss will often lead to errors in the measurment. In order to prevent evaporative loss, the relative humidity of the room must be kept very high. In addition, a highly accurate analytical balance must be used for this kind of measurement.

The proper type of equipment and operating environment which are needed to make gravimetric verification of automated pipetting devices are usually not available in a clinical laboratory. Even if these equipment were available, the skill level and time required to conduct these measurements are very high. Thus, the gravimetric verification of the volumetric accuracy of the robotic ELISA processing devices is not practical in a clinical laboratory.

Typically, in the prior art, colorimetric reagents have been used to verify the volume delivered by a liquid transfer device. In these cases the volume of the reagent is usually calculated by the following equation. (Beer's Law):

$$A = abc$$

where
A = absorbance measured
a = molar absorptivity
b = path length (usually fixed for a given instrument)
c = concentration of colorimetric reagent.

Using this common approach, the measured volume is dependent on the absolute concentration of the reagent. Therefore, the approach requires that the exact concentration of the reagent is known.

In reality the concentration of the colorimetric reagent, cannot be precisely controlled. Therefore, verification methods that calculate volume directly from the absorbance measured are often inaccurate. Another verification method is justified in U.S. Pat. No. 4,354,376 issued to Greenfield et al. According to Greenfield et al, "In carrying out the invention, a kit is provided comprising a vial of a standard calibration solution of a first predetermined color density, a vial of a standard calibration solution of a third predetermined color density, a calibration vial containing a predetermined volume of a diluent, and one or more vials or bottles, each containing a solution of a calibration reagent of a different color density. The kit may also contain a pipette calibration chart on which spectrophotometer readings of the light adsorption by the solutions in the standard calibration vials are plotted to provide a reference curve can be used to determine the volume of the calibration reagent pipetted into a calibration vial to replace an equal volume of diluent removed therefrom. That volume is the volume of the pipette being calibrated".

The difficulty with Greenfield et al is a manual procedure apparently used for the occasional pipette that needs to be calibrated. It is not at all suitable for a method that contemplates calibrating an automated device.

SUMMARY OF THE INVENTION

Many of the disadvantages of the prior art dispenser verification systems are overcome by the method of this invention. According to this invention, a method of determining the accuracy of a liquid dispensing pipet using a plurality of wells of the same configuration and volume is accomplished by the steps of: introducing a known volume of a colorimetric reagent that absorbs radiant energy in a manner directly proportional to the concentration into a first well, dispensing a desired volume of the colorimetric reagent using the liquid dispensing pipette into a second one of the wells, measuring the absorbance of the reagent in each of the wells, calculating actual volume of reagent dispensed in the second well by multiplying the known volume by the ratio of the absorbance of reagent in the second well to the absorbance of the reagent in the first well.

In a preferred embodiment the calculated actual volume as compared to the desired volume furthermore the wells are disposed in rows and columns and the known volume of colorimetric reagent introduced into each well of the first two of wells, the absorbance of each well of the first row is averaged to obtain an average absorbance, and the actual volume is calculated using the average absorbance of the first row of wells.

In a preferred embodiment of the invention the colorimetric reagent is cobalt sulfate. In the further embodiment of the method of this invention additional rows of wells wherein additional rows of wells are each dispensed with the desired volume of different concentration of the colorimetric reagent calculating the actual volume of each of the different desired volumes dispensed by multiplying the known volume by the ratio of the absorbance of reagent in each dispensed well to the average absorbance of the first row of wells.

By the use of this invention and its unique way of measuring the volume delivered the need for a colorimetric reagent with a precisely known absorbance value is eliminated. Instead of calculating the volume delivered directly from a measured absorbance value, the volume is calculated from a ratio of the absorbance values for a sample delivered by a precisely calibrated pipet and a sample delivered by the automated device thus the error introduced by the variations in concentrations of the reagent is significantly reduced.

BRIEF DESCRIPTION OF THE DRAWINGS

The invention may be more fully understood from the following detailed description thereof taken in connection with accompanying drawings which form a part of this application and in which.

DETAILED DESCRIPTION OF THE PREFERRED EMBODIMENT OF THE METHOD

Figure 1:
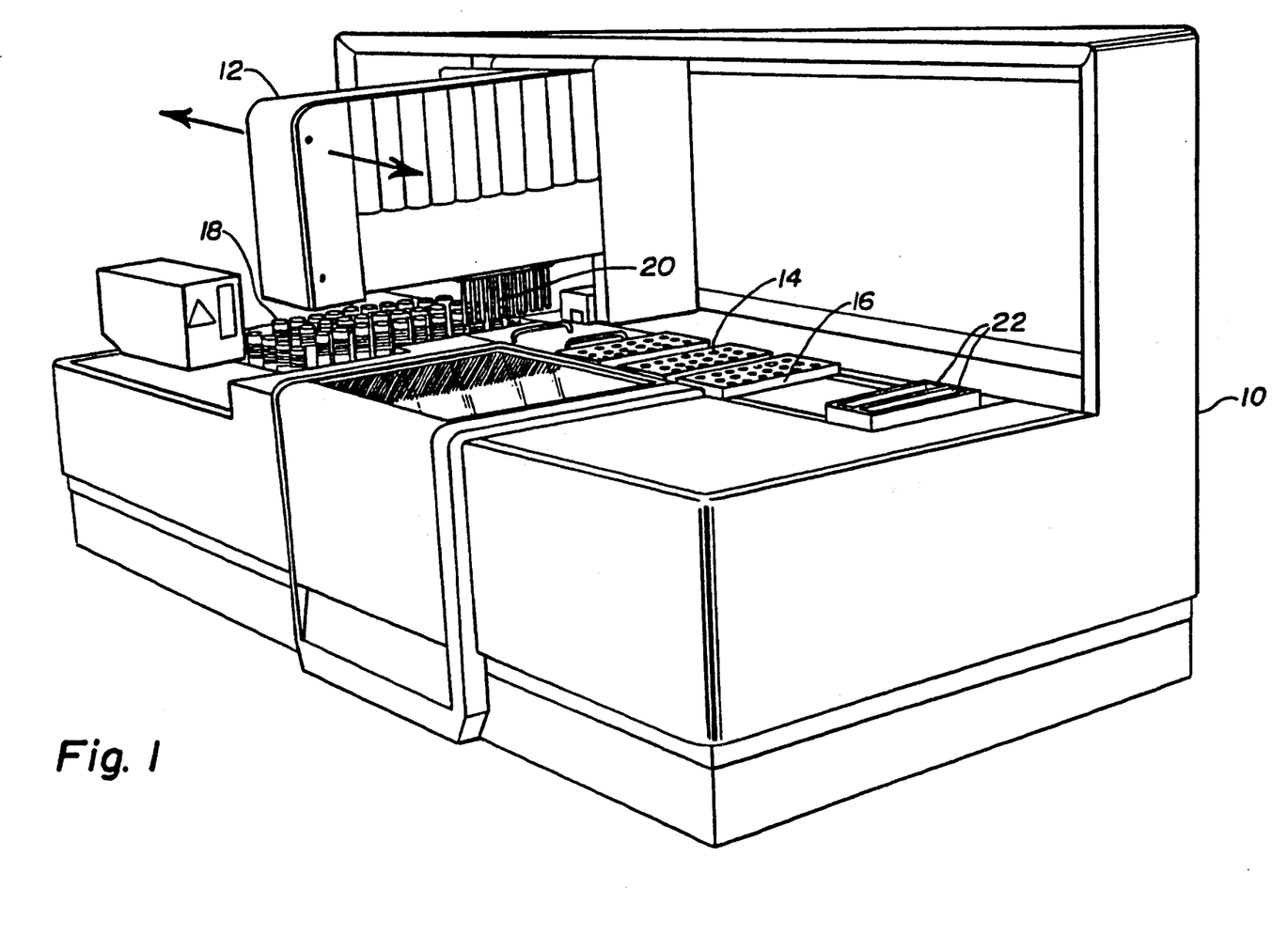
FIG. 1 is a pictorial view of a SUMMIT TM sample transfer system having a robotic arm for effecting the transfer of samples and reagents to microtiter plates for reaction and measurement.

The method of this invention preferably is used with the SUMMIT TM Automated Transfer System sold by E. I. Du Pont de Nemours and Company, Wilmington, Del. and the invention will be described in that context. The SUMMIT TM system includes a robotic type instrument 10 (FIGS. 1 and 2) in which a robotic arm 12 transfers selected volumes of liquid (reagents, diluents and samples) to wells 14 in microtiter plates 16. The wells 14 are typically arranged in rows and columns to form typically an $8 \times 12$ assay of wells 14. The samples to be processed are held in a certain rack location 18. An array of pipettes 20 mounted on the robotic arm 12 can withdraw samples from the sample locations and transfer them to the wells 14 of microtiter plates 16. Adjacent to the microtiter plates 14 (microplate) are reagent and diluent reservoirs 22.

Figure 3:
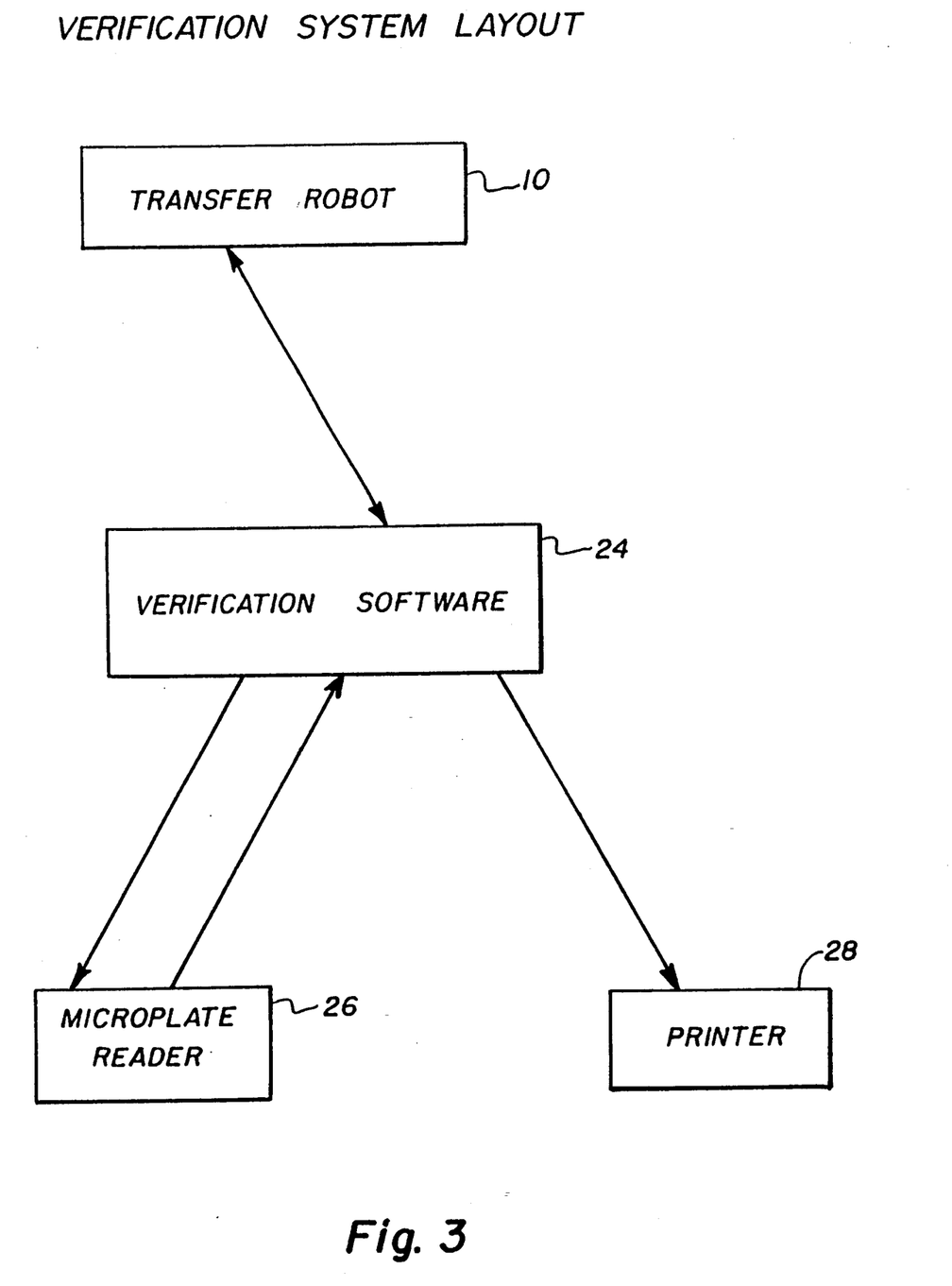
FIG. 3 is a block diagram depicting the interaction of the software, used in the method of the inventor, with SUMMIT TM instrument; describes the equipment utilized to perform the method of this invention.
Figure 4A:
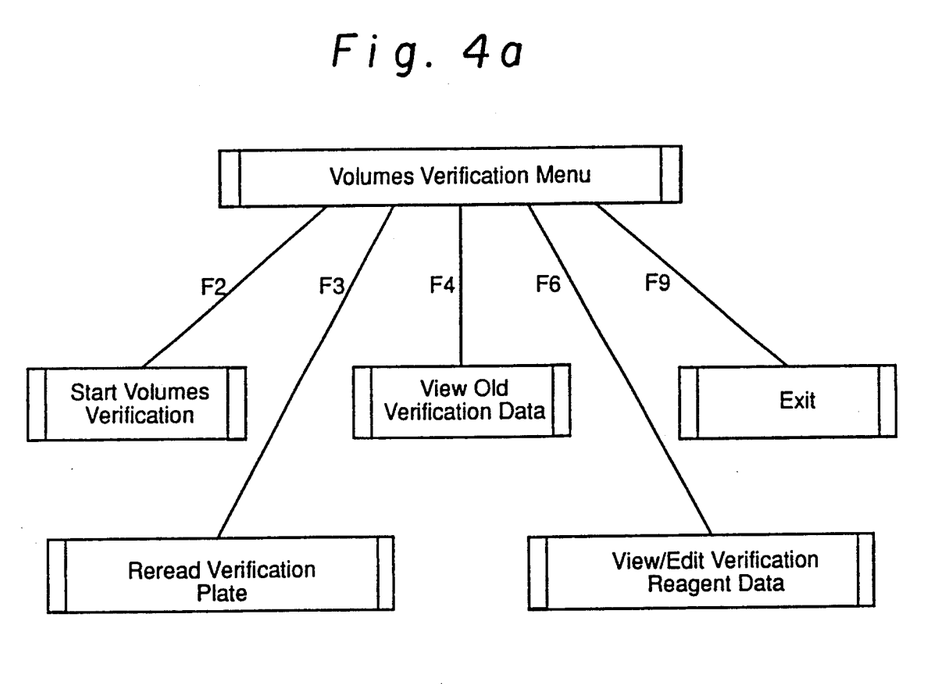
FIGS. 4a-4i are flow charts of the software used to implement the method of this invention.
Figure 4B:
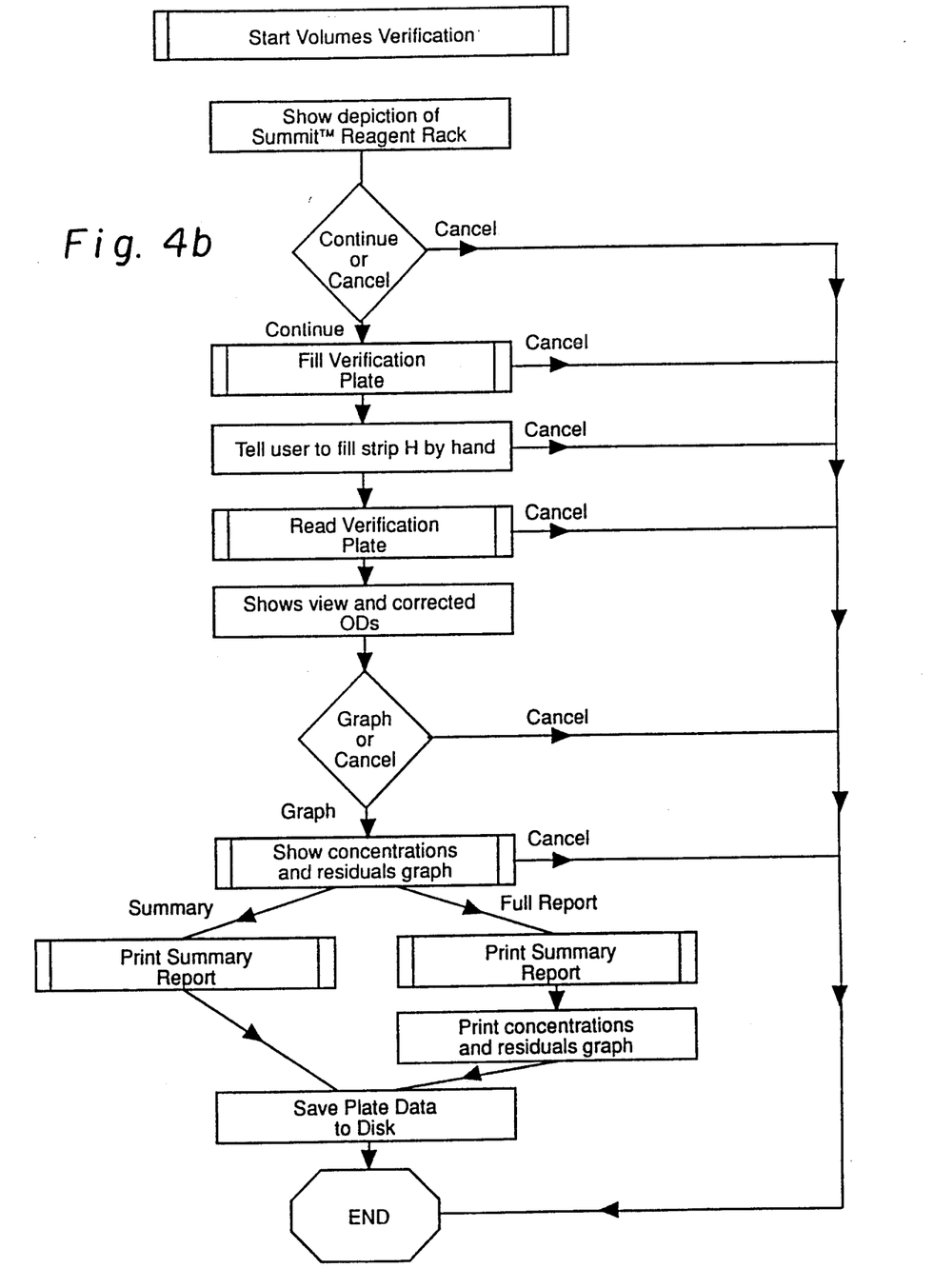
Figure 4C:
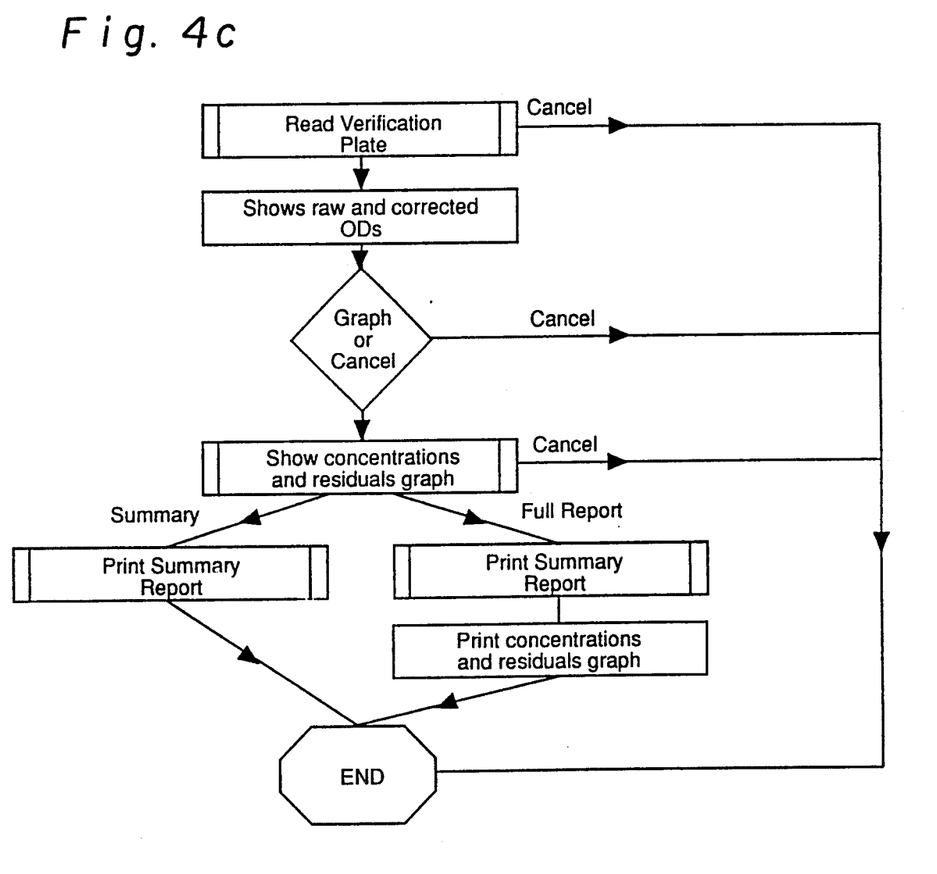
Figure 4D:
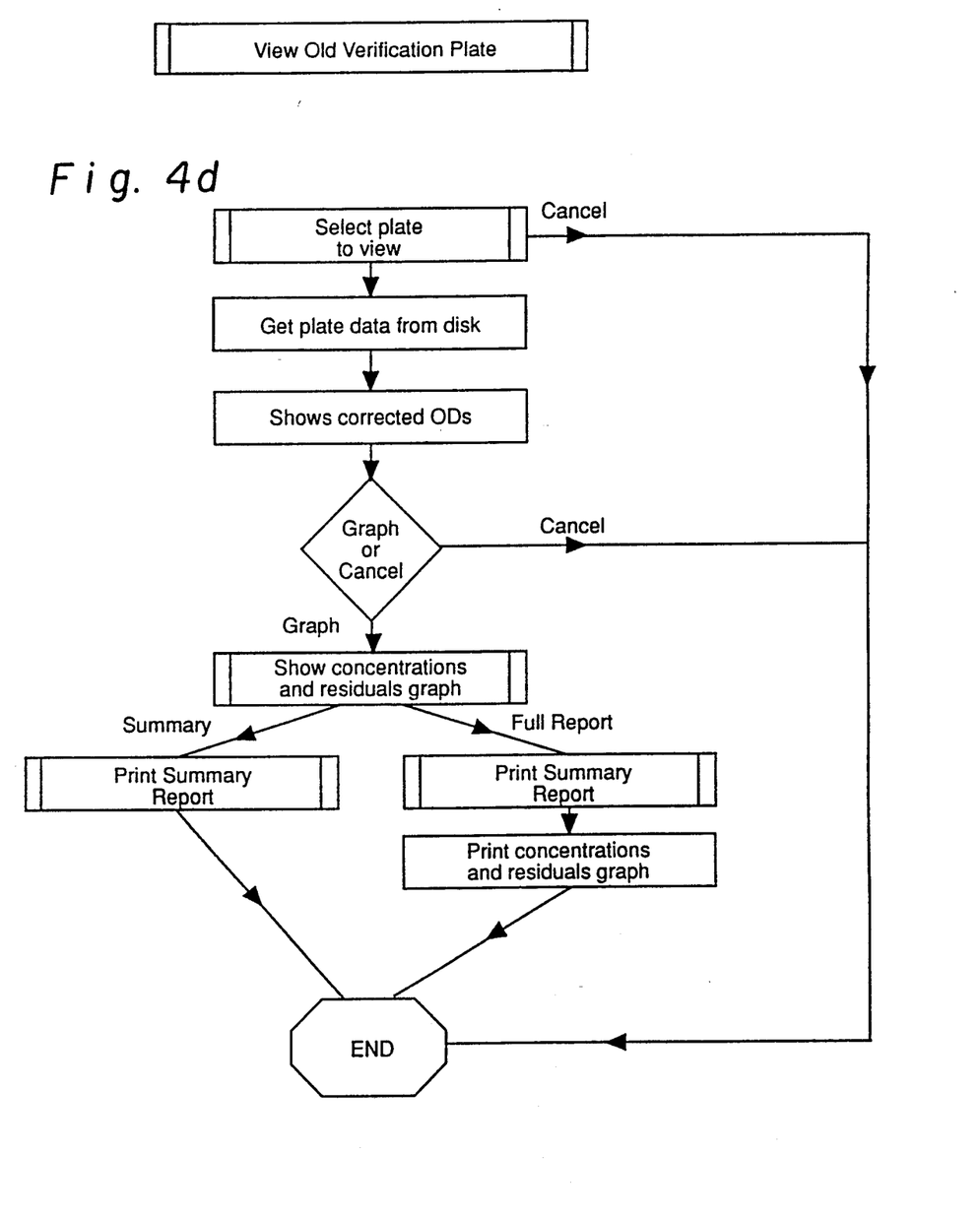
Figure 4E:
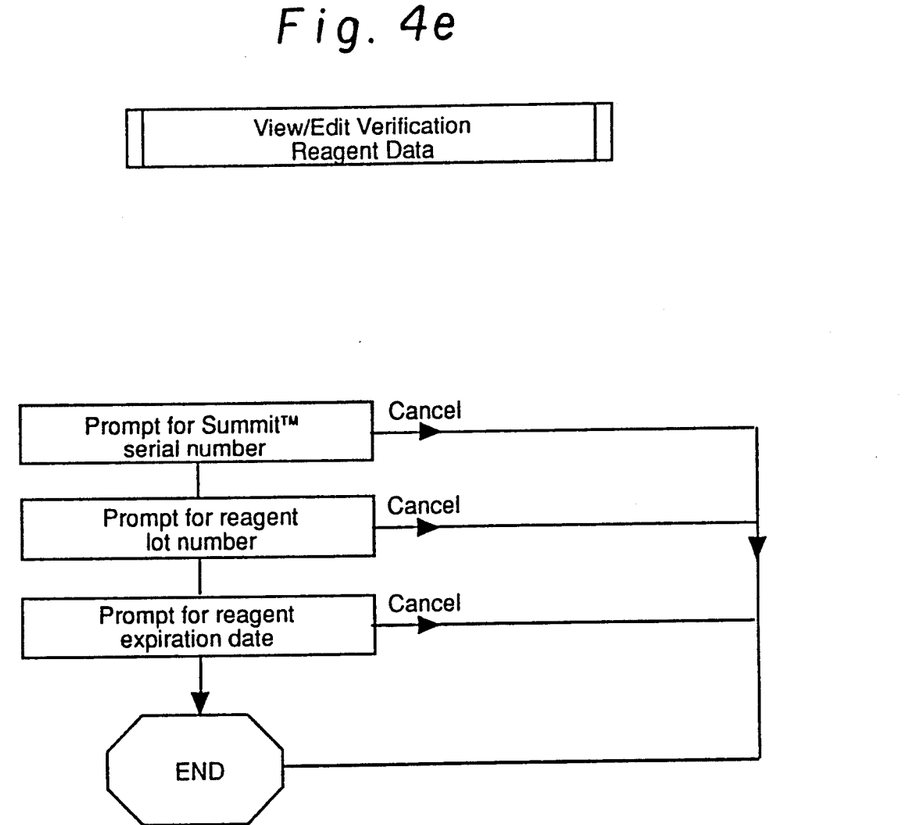
Figure 4F:
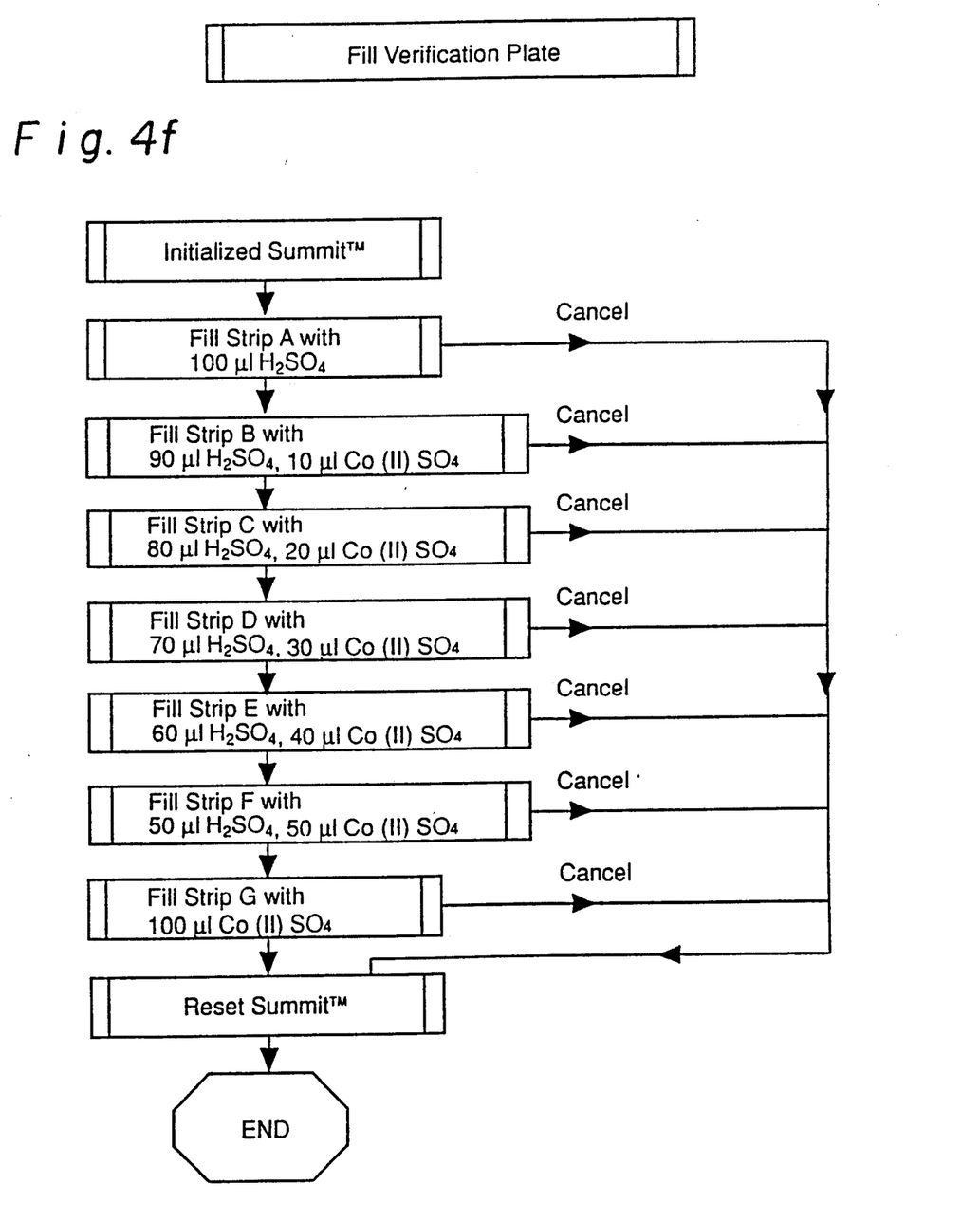
Figure 4G:
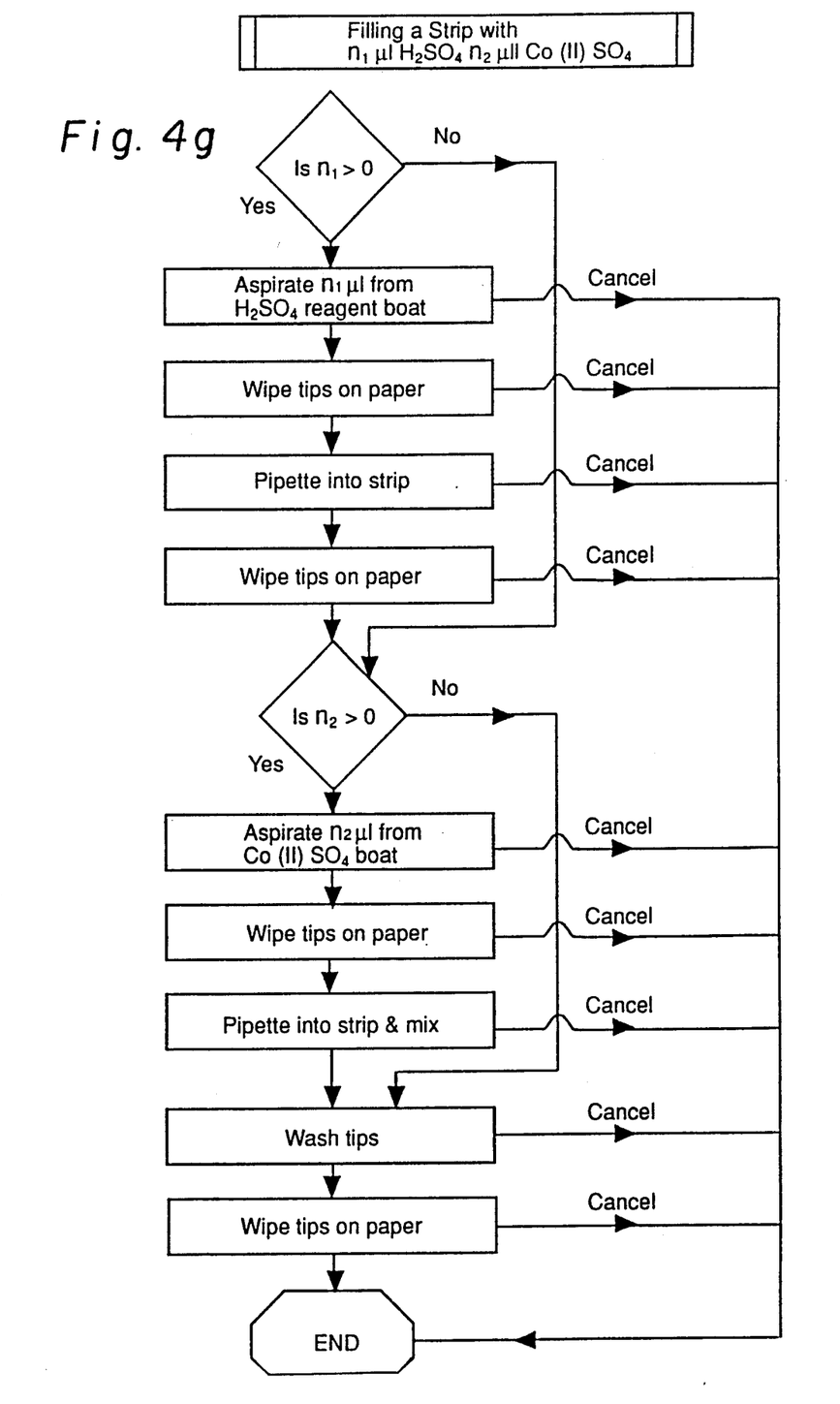
Figure 4H:
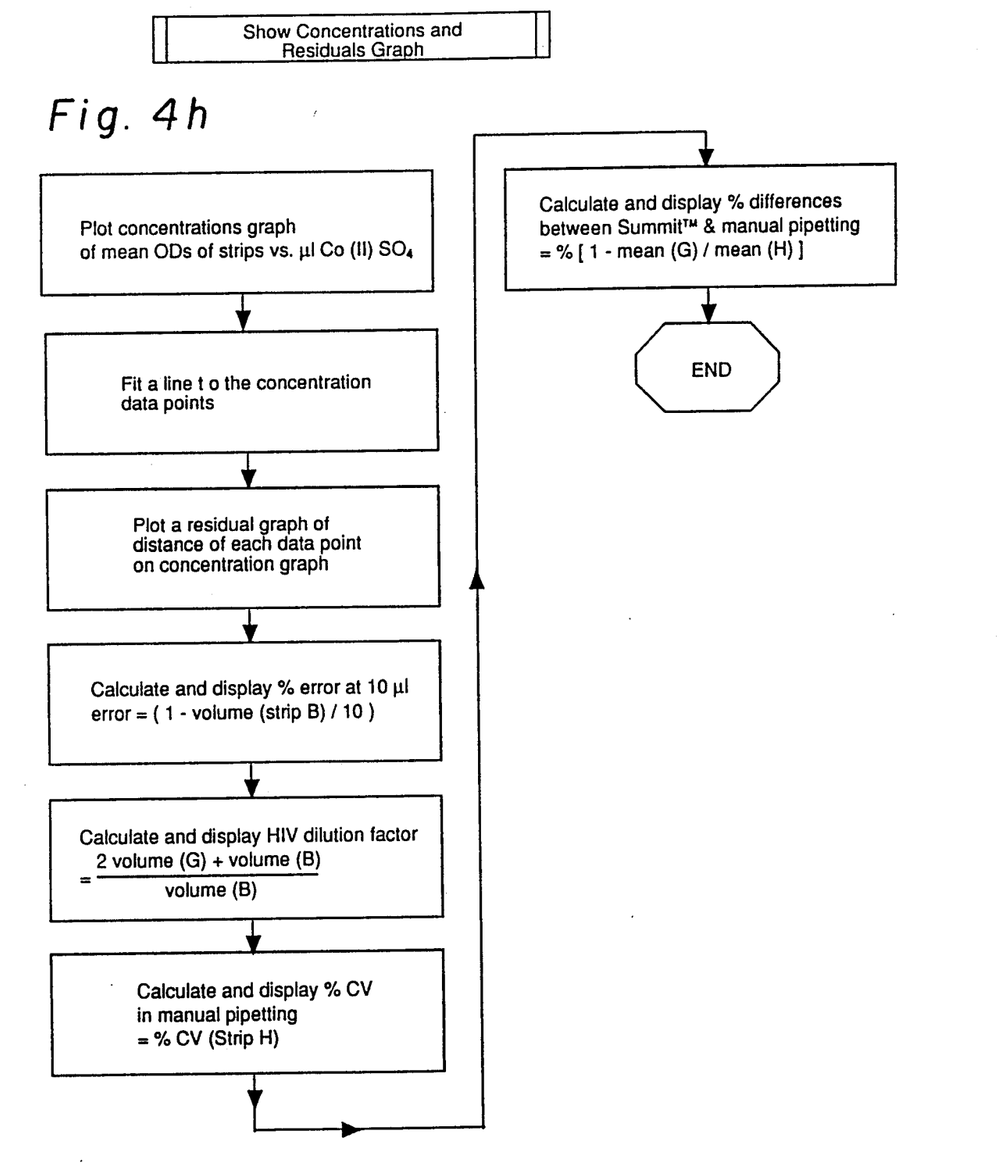
Figure 4I:
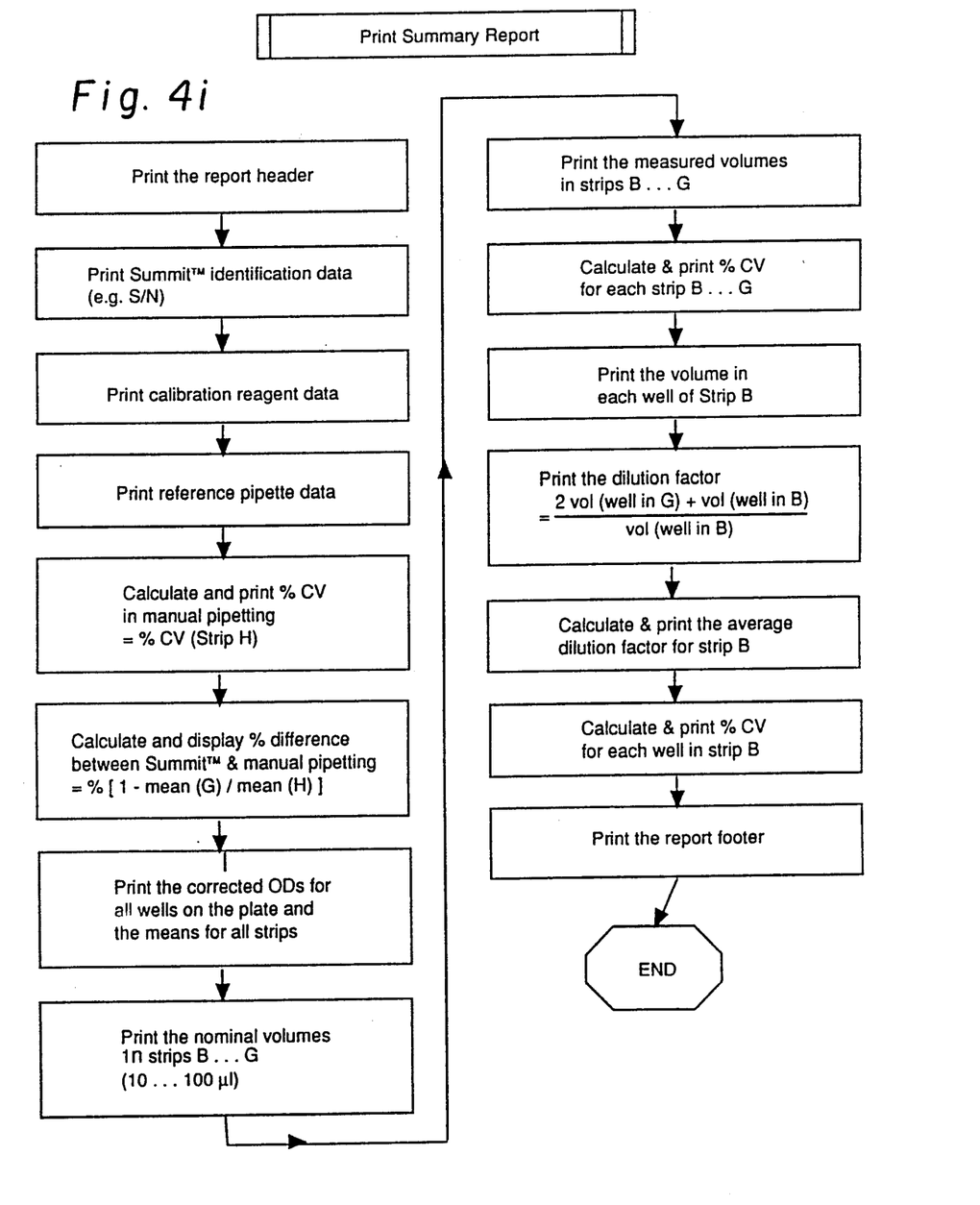

Referring to FIG. 3 it is seen that the SUMMIT TM instrument includes verification software 24 which operating in conjunction with a microplate reader 26 measures the absorbance of a colorimetric reagent of different concentrations in each of the wells of the microplate 14. For this purpose a colorimetric reagent is used. Such colorimetric reagent may be any of those stable reagents well known in the art that follow Beer's Law. These include cobalt sulfate and potassium dichromate, with cobalt sulfate being preferred. When cobalt sulfate is used, sulfuric acid is used as a diluent to maintain stability of the reagent. The software performs a routine in which the pipetting arms 20 dispense different concentrations of the reagent in the several wells 14 (usually row by row), the concentration of each well is measured, and result printed out in the form of reports at the printer 22 stating the accuracy of the dispensed material.

In accordance with the invention, instead of calculating the volume delivered directly from the measured absorbance value, the volume is calculated from a ratio of the absorbance values for a sample delivered by a precisely calibrated pipette and a sample delivered by the automated device. Thus, the error introduced by variations in the concentration of the reagent is eliminated. Using this common approach, the measured volume is dependent on the absolute concentration of the reagent. Therefore, the approach requires that the exact concentration of the reagent is known.

A preferred method to prepare a reference solution "knowing" the exact concentration is containing the colorimetric reagent which preferably is calibrated by a gravimetric method. The gravimetric method includes determining the volume based on weight measurements. The actual volume (V) delivered (in uL) equals:

$$V = 1000 \text{ (uL/mL)} \times \text{weight (g)} \times \text{volume factor (mL/g) (at the appropriate temperature)}$$

The volume factor is the volume of 1.000 g of pure water at that given temperature.

For Example:

The volume factor at 23° C. is 1.0035 mL/g. If the weight of the water delivered is equal to 0.10001 g at 23° C., the volume delivered is:

$$V = 1000 \text{ uL/mL} \times 0.10001 \text{ g} \times 1.0035 \text{ mL/g} = 100.36 \text{ uL}$$

The calibrated volume of the reference pipette should be calculated from the average of at least ten weight measurements using a calibrated analytical balance. This reference volume typically is introduced manually into each well 14 of a row of one of the micro-plates, which is typically twelve wells.

The instrument control software as will be described instructs the instrument to fill the micro-plate as follows:

a) Dispensing of Reagent for Blank-Absorbance Correction

The first row of wells (A1–A12) (see table below) will be filled with 1% sulfuric acid and will be used to calculate the blank absorbance. The blank absorbance is the average of wells A1–A12.

b) Volume and Calculations

To measure the volume dispensed at 10 uL, the second row of wells (B1–B12) are first filled with 90 uL of 1% sulfuric acid. Then 10 uL of the Cobalt Sulfate reagent are dispensed into the 1% sulfuric acid and the two reagents are mixed by moving the plunger of the pipet dispenser (included in robotic arm 12) up and down several times.

This mode of dispensing ensures that the colorimetric reagent is completely dispensed. When attempts are made to dispense a 10-uL droplet of liquid onto a "dry" microtiter plate, the surface tension on the droplet will cause the liquid to adhere to the tip of the pipet and consequently prevent a complete transfer of the reagent.

To ensure that volumes other than 10 uL are also accurately dispensed, the rest of the microtiter plate is filled with different volumes of the colorimetric reagent Cobalt Sulfate and its diluent 1% sulfuric acid as summarized below:

| Row | uL $H_2SO_4$ | uL $CoSO_4$ | Comment |
| --- | --- | --- | --- |
| A1–A12 | 100 uL | 0 uL | Blank by SUMMIT |
| B1–B12 | 90 | 10 | dispensed by SUMMIT |
| C1–C12 | 80 | 20 | dispensed by SUMMIT |
| D1–D12 | 70 | 30 | dispensed by SUMMIT |
| E1–E12 | 60 | 40 | dispensed by SUMMIT |
| F1–F12 | 50 | 50 | dispensed by SUMMIT |
| G1–G12 | 0 | 100 | dispensed by SUMMIT |
| H1–H12 | 0 | 100 | by reference pipette |

The software assumes that
 i) The volume pipetted into wells H1–H12 is correct. These wells are pipetted manually using a calibrated pipet.
 ii) The absorbance (A) of Cobalt Sulfate, in 1% sulfuric acid, is directly proportional to its concentration (Beer's Law).

Therefore, the volume of Cobalt Sulfate solution (V) delivered to each well is calculated as:

$$V = (\text{Absorbance measured/Av Absorbance H1-H12}) \times \text{Volume of Calibrated Pipette}$$

The software also allows for the correction of the error in the reference pipet. The calculated volume is compared with the gravimetrically calibrated volume instead of the nominal volume of the reference pipet as shown in the above equation. To obtain absorbance measurement of the cobalt sulfate reagent, the filled microtiter plate is read at 492 nM.

Software of this invention performs all the necessary data collection and calculations. A report is generated and a sample report is attached. The details of the software may be best understood from the flow chart of FIG. 3.

SYSTEM SOFTWARE

The IBM Computer (IBM AT or IBM PS2/50) interfaces with the SUMMIT TM and an automatic microplate reader through two separate serial interface ports.

The software program sends command sequences to the SUMMIT controller electronics, effectuates the pipetting of samples and receives absorbance data from the microplate reader.

SYSTEM OPERATION

Figure 2:
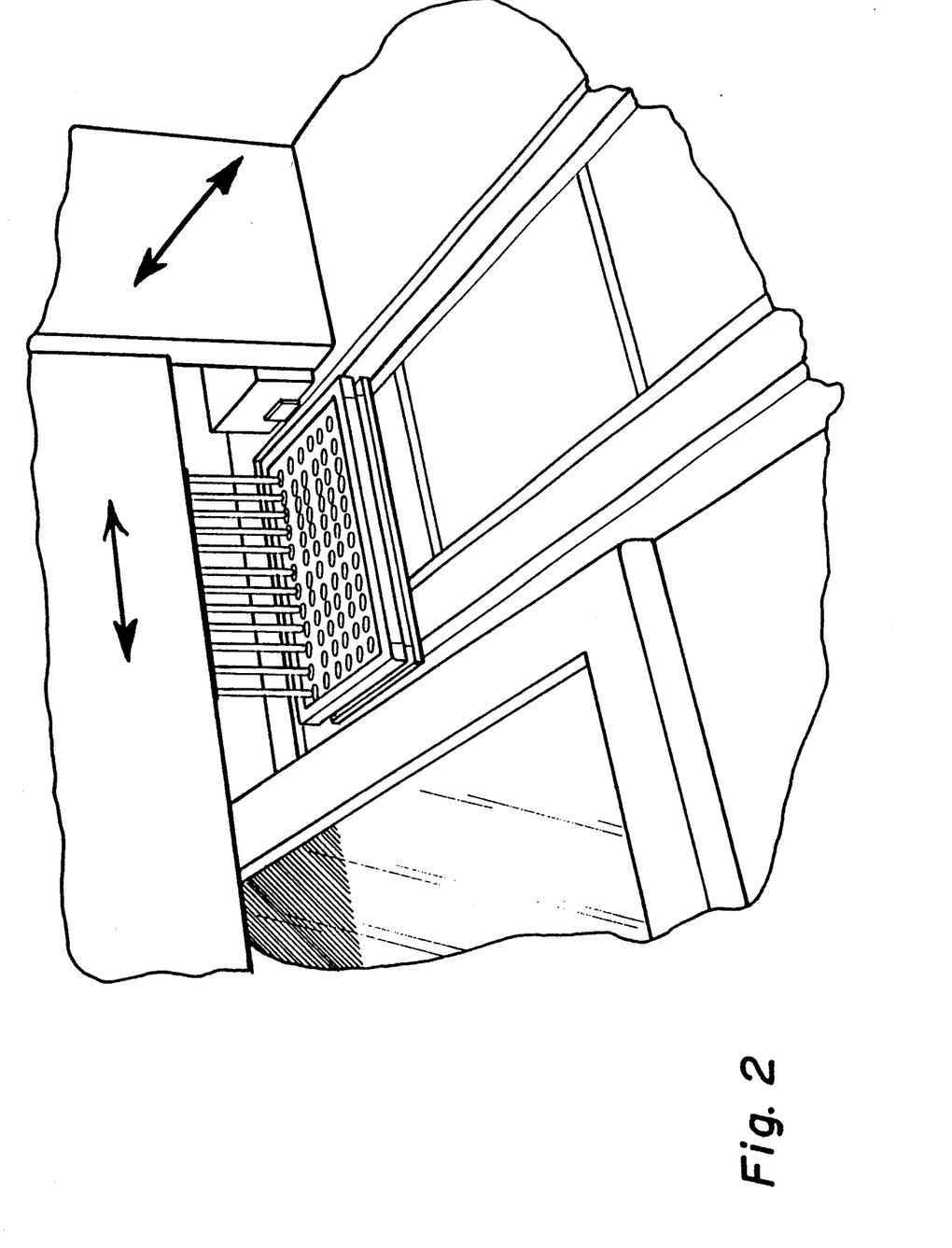
FIG. 2 is a fragmentary pictorial view of the robotic arm of FIG. 1.

To begin the verification process, the user will access the software program and select the "Volumes Verification Menu" (FIG. 2.a). Normally the user will then select the "Start Volumes Verification" option.

The software program is interactive and instructs the user to perform certain tasks during the verification process. For example, the software program will instruct the user to place the appropriate reagents at the proper locations by showing a depiction of the SUMMIT TM reagent rack (FIG. 2.b). If the user wishes to stop the procedure, he may choose the "cancel" option at any time. The junctions for the "cancel" options are shown in FIGS. 2.b to 2.g.

After the reagents are placed in the correct locations, the user will continue the verification process by selecting the "Fill Verification Plate" option. A series of commands will be sent to the SUMMIT and strips A through G will be filled automatically.

When rows of wells A through G are completely filled, the SUMMIT instrument will stop and the software program will tell the user to fill strip H with a calibrated reference pipet. Once this step is completed, the user will place the microtiter plate into the microtiter reader by selecting the "Read Verification Plate" option. Data collection will be performed automatically and the data will be displayed on the screen. If an error occurs during the data collection step, the user has the option to repeat the data collection process by selecting the "Reread Verification Plate" option (FIG. 2.c). Various calculations will be performed and the user has the option to print a summary report or a full report with graphs. Data will be saved automatically on the system hard-disk and can be recalled anytime by selecting the "View Old Verification Plate" option (FIG. 2.d).

For record keeping purposes, the user will store the serial number of the SUMMIT, the reagent lot number and the reagent expiration date in the system by using the "View/Edit Verification Reagent Data" option (FIG. 2.e).

INSTRUMENT CONTROL AND CALCULATIONS

Details for the instrument control functions of the software program are shown in FIGS. 2.f and 2.g. During the "Initialize SUMMIT" step, commands wil be sent to the SUMMIT to find the starting position for the stepper motors. Twelve disposable pipet tips will then be loaded and the plate will be filled automatically. The user may choose to abort the filling process at anytime by selecting the cancel option. Details of the filling procedure for individual strips are shown in FIG. 2.g. During the process of filling each strip, the software program will instruct the SUMMIT to aspirate the reagent, wipe the tips and pipette the reagent into the microtiter plate. The amounts of cobalt sulfate and sulfuric acid required for each strip are shown in FIG. 2.f. Details of the calculation algorithm and the report printing format are shown on FIGS. 2.h and 2.i, respectively.

The method described is a relatively simple yet highly accurate means for determining the accuracy of the automatic dispensing pipets. It does not rely upon the accuracy of a particular reagent but rather relies upon comparisons made to a reference.

We claim:

1. A method of determining the accuracy of a liquid dispensing pipette using a plurality of wells of the same configuration and volume by the steps of:

using a precisely calibrated pipette, introducing a known volume of a colorimetric reagent of a known concentration that absorbs radiant energy in a manner directly proportional to the colorometric reagent concentration in a first one of said wells, dispensing a first desired volume of the colorimetric reagent using the liquid dispensing pipet into a second one of said wells, measuring absorbance of the reagent in each of the wells, and calculating an actual volume of reagent dispensed in the second well by multiplying the known volume by the ratio of the absorbance of reagent in the second well to the absorbance of the reagent in the first well.

2. The method of claim 1 which includes an additional step of comparing the calculated actual volume with the desired volume.

3. The method of claim 1 wherein the colorimetric reagent is either cobalt sulfate or potassium dichromate.

4. The method of claim 1 which includes additional steps of dispensing a second desired volume of the colorimetric reagent together with a first desired volume of a diluent for the reagent into a third well, and calculating the actual volume of reagent dispensed in the third well by multiplying the known volume by the ratio of the absorbance of the reagent in the third well to the absorbance of the reagent in the first well.

5. In the method of claim 4 wherein the diluent is sulfuric acid.

6. In the method of claim 2 which includes additional steps of dispensing a second desired volume of the colorimetric reagent together with a first desired volume of a diluent for the reagent into a third well, and calculating the actual volume of reagent dispensed in the third well by multiplying the known volume by the ratio of the absorbance of the reagent in the third well to the absorbance of the reagent in the first well.

7. In the method of claim 6 wherein the colorimetric reagent is cobalt sulfate.

8. In the method of claim 3 wherein additional rows of wells are each dispensed with desired volumes of different concentrations of the colorimetric reagent, calculating the actual volume of each of the different desired volumes dispensed by multiplying the known volume by the ratio of the absorbance of reagent in each dispensed well to the average absorbance of the first row of wells.

* * * * *

UNITED STATES PATENT AND TRADEMARK OFFICE
CERTIFICATE OF CORRECTION

PATENT NO. : 5,061,639
DATED : October 29, 1991
INVENTOR(S) : Kaki R. Lung, John S. Fok, and Alex J. Chanin It is certified that error appears in the above-identified patent and that said Letters Patent is hereby corrected as shown below:

On the title page, box [75], labeled "Inventors" delete "John S. Fox" and insert ---John S. Fok---

Signed and Sealed this

Sixteenth Day of March, 1993

Attest:

STEPHEN G. KUNIN

*Attesting Officer*   Acting Commissioner of Patents and Trademarks